(12) United States Patent
Truwit et al.

(10) Patent No.: US 12,290,390 B2
(45) Date of Patent: May 6, 2025

(54) AUTOMATED SCOUT SCAN EXAMINATION

(71) Applicant: KONINKLIJKE PHILIPS N.V., Eindhoven (NL)

(72) Inventors: Charles Loeb Truwit, Wayzata, MN (US); Rolf Juergen Weese, Norderstedt (DE); Guenter Zeitler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 439 days.

(21) Appl. No.: 17/797,121

(22) PCT Filed: Jan. 26, 2021

(86) PCT No.: PCT/EP2021/051742
§ 371 (c)(1),
(2) Date: Aug. 3, 2022

(87) PCT Pub. No.: WO2021/156105
PCT Pub. Date: Aug. 12, 2021

(65) Prior Publication Data
US 2023/0067146 A1    Mar. 2, 2023

Related U.S. Application Data

(60) Provisional application No. 62/971,323, filed on Feb. 7, 2020.

(30) Foreign Application Priority Data

Feb. 17, 2020    (EP) .................................... 20157670

(51) Int. Cl.
*A61B 6/00*    (2024.01)
*A61B 6/46*    (2024.01)
*G06T 7/10*    (2017.01)

(52) U.S. Cl.
CPC .............. *A61B 6/488* (2013.01); *A61B 6/463* (2013.01); *A61B 6/54* (2013.01); *G06T 7/10* (2017.01);
(Continued)

(58) Field of Classification Search
CPC ........... A61B 6/488; A61B 6/463; A61B 6/54; A61B 6/032; A61B 5/0037; A61B 5/055;
(Continued)

(56) References Cited

U.S. PATENT DOCUMENTS

2006/0239544 A1    10/2006    Yankelevitz et al.
2013/0021030 A1    1/2013    Zuehlsdorff et al.
(Continued)

FOREIGN PATENT DOCUMENTS

WO        2019120014 A1    6/2019

OTHER PUBLICATIONS

S. A. Tuncel, B. Çağlı, A. Tekataş, M. Y. Kırıcı, E. Ünlü, H. Gençhellaç; Extraspinal Incidental Findings on Routine MRI of Lumbar Spine: Prevalence and Reporting Rates in 1278 Patients; Korean J Radiol 2015, 16(4), 866-873.
(Continued)

*Primary Examiner* — Wassim Mahrouka (57) ABSTRACT

Disclosed herein is a medical system (100, 300, 400) comprising a memory (110) storing machine executable instructions (120). The medical system further comprises an anatomical detection module (122). The anatomical detection module is configured for detecting an anatomical deviation in response to inputting tomographic medical scout image data (124). The anatomical detection module is configured for outputting a localization (126) of the anatomical deviation in the tomographic medical scout image data if the anatomical deviation is detected. The medical system further comprises a processor (104) configured for controlling the
(Continued)

medical system. Execution of the machine executable instructions causes the processor to: receive (200) the tomographic medical scout image data, receive (202) the localization of the anatomical deviation from the anatomical detection module in response to inputting the tomographic medical scout image data into the anatomical detection module, and provide (204) a warning signal (128) if the localization is received.

14 Claims, 7 Drawing Sheets

(52) U.S. Cl.
CPC .............. *G06T 2207/10072* (2013.01); *G06T 2207/20081* (2013.01); *G06T 2207/20084* (2013.01)

(58) Field of Classification Search
CPC ....... A61B 5/7267; A61B 6/5211; G06T 7/10; G06T 2207/10072; G06T 2207/20081; G06T 2207/20084; G16H 40/63; G16H 30/20
See application file for complete search history.

(56) References Cited

U.S. PATENT DOCUMENTS

| 2017/0293734 A1 | 10/2017 | Potter et al. |
| 2018/0250466 A1 | 9/2018 | Bode |
| 2018/0268569 A1 | 9/2018 | Kroell |
| 2019/0320934 A1 | 10/2019 | Odry et al. |

OTHER PUBLICATIONS

R. George, J. Dela Cruz, R. Singh, R. Ilangovan; MRIMASTER.com; https://mrimaster.com/PLAN%20L%20SPINE.html (downloaded Jul. 21, 2022).
O. Ronneberger, P. Fischer, T. Brox; U-Net: Convolutional Networks for Biomedical Image Segmentation. Proc. MICCAI 2015. Lecture Notes in Computer Science, vol. 9351, 234-241.
S.M. Anwar, M. Majid, A. Qayyum, et al.; Medical Image Analysis using Convolutional Neural Networks: a Review; J Med Syst 2018, 42, 226.
L. He, Z. Peng, B. Everding, X. Wang, C. Y. Han, K. L. Weiss, W. G. Wee; A comparative study of deformable contour methods on medical image segmentation; Image and Vision Computing 2008, 26, 141-163 .
International Search Report and Written Opinion from PCT/EP2021/051742 mailed Apr. 28, 2021.
Booth et a; "Management of Incidental Findings During Imaging Research in Healthy Volunteers: Current UK Practice" The British Journal of Radiology, 85 (2012) p. 11-21.

AUTOMATED SCOUT SCAN EXAMINATION

CROSS REFERENCE TO RELATED APPLICATIONS

This application is a U.S. national phase application of International Application No. PCT/EP2021/051742 filed on Jan. 26, 2021, which claims the benefit of U.S. Provisional Application Ser. No. 62/971,323 filed Feb. 7, 2020 and EP Application Serial No. 20157670.9 filed on Feb. 17, 2020, each of which is incorporated herein by reference.

FIELD OF THE INVENTION

The invention relates to medical imaging, in particular to scan planning for tomographic medical imaging modalities.

BACKGROUND OF THE INVENTION

In tomographic medical imaging modalities such as magnetic resonance imaging or computed tomography the internal anatomical structure of a subject may be imaged. During a tomographic medical imaging procedure, the region of interest to be imaged is typically located using a so-called scout scan or localizer scan. The scout scan is acquired for a low resolution and/or high signal to noise to quickly locate the region of interest. After the region of interest is located in the scout scan acquired then the operator or automated algorithm configures the medical imaging system to acquire a more detailed clinical scan.

United States patent application US 2017/0293734 discloses a system for identifying significant incidental findings from medical records. In one example embodiment, an example computing device receives a medical report and derives a textual component from the medical report. The computing device then identifies one or more medical findings from the textual component and determines a clinical context for each of the one or more medical findings. The computing device then identifies one or more clinical cues from the one or more medical findings and generates one or more condition signals from the one or more clinical cues. The computing device then generates a condition alert from the one or more condition signals. The condition alert is indicative of a significant incidental finding. Using various embodiments contemplated herein, significant incidental findings can be identified for follow-up by a user.

SUMMARY OF THE INVENTION

The invention provides for a medical system, a computer program product and a method in the independent claims. Embodiments are given in the dependent claims.

A scout scan, also described herein as a tomographic medical image data, is used to position the region for which clinical tomographic medical image data is acquired. The scout scan will have a lower resolution and/or lower signal to noise than the clinical tomographic medical image data so that it may be acquire rapidly. The tomographic medical scout image data is also acquired for a first region and the clinical tomographic medical image data is acquired for a second region. The second region is within the first region. The tomographic medical scout image data therefore images anatomical structures that are not within the second region. If there are anatomical abnormalities within the first region, but outside of the second region then they may go unnoticed. The tomographic medical scout image data may not be of a sufficient quality to enable a human to finally assess any anatomical abnormalities.

Embodiments may provide for an improved medical system that uses an anatomical detection module which can be used to automatically detect and localize anatomical abnormalities in tomographic medical scout image data. Such a system may for example be used to examine a high volume of scout images as well as detect anatomical abnormalities that would be difficult for a human to detect. For example, discrepancies in the relative size of organs may not be noticeable to a human. In other examples tumors, growths, or other irregularities may be too obscured by noise or low resolution to be detectable.

In one aspect the invention provides for a medical system that comprises a memory storing machine-executable instructions. The medical system further comprises an anatomical detection module. The anatomical detection module may for example be a software or machine-executable component which is also stored on the memory. In other examples the anatomical detection module may be a discreet or separate computational device. The anatomical detection module is configured for detecting an anatomical deviation in response to inputting a tomographic medical scout image data. The detection comprises outputting a localization of the anatomical deviation in the tomographic medical scout image data. The tomographic medical scout image data may for example be image data that is either two or three-dimensional.

The tomographic medical scout image data may also be of a lower resolution than images used for providing a diagnosis or providing diagnostic images. The localization of the anatomical deviation may for example be an indication of a position of the anatomical deviation. In some examples this may be a location which contains at least part of the anatomical deviation, in other examples it may be a segmentation or a bounding box. An anatomical deviation may for example be a growth or structure which is not part of a normal subject. For example, a tumorous growth may be an example of an anatomical deviation. In other examples the anatomical deviation may be an anatomical structure which has a size or position or boundary that deviates from a particular normal range. For example, an organ could have an irregular boundary; it could have additional structures or growths within it. The anatomical deviation may also indicate that the size of a particular organ or anatomical region is larger or small than would be expected in relation to other anatomical structures within the subject.

The medical system further comprises a processor configured for controlling the medical system. In various examples the medical system may take different forms. In some examples the medical system may be a computational device such as a workstation used by medical professionals to examine radiological data. In other examples the medical system may be a component possibly located remotely or in the cloud which provides processing of medical image data. In yet other examples the medical system may also comprise a tomographic medical imaging system or scanner.

Execution of the machine-executable instructions causes the processor to receive the tomographic medical scout image data. It may be received in different ways in different examples. In some examples the tomographic medical scout image data may be retrieved from a storage device that is part of the medical system. In other examples the tomographic medical scout image data may be received via a network connection or via an external data carrier. In yet other examples the tomographic medical scout image data may be received by controlling a tomographic medical imaging system.

Execution of the machine-executable instructions further causes the processor to receive the localization of the anatomical deviation from the anatomical detection module in response to inputting the tomographic medical scout data into the anatomical detection module.

Execution of the machine-executable instructions further causes the processor to provide a warning signal if the localization is received. This warning signal may take different forms in different examples. In some examples the warning signal may be a display or indicator on a screen of the medical system itself. For example, the medical system may be a terminal or workstation controlling a tomographic medical imaging system. In this case the warning signal may alert the operator that an anatomical deviation in one of the tomographic medical scout image data has been detected. This may enable the operator of the medical system to rapidly determine if further scans are needed. This for example may be of benefit to an operator who is untrained in looking at tomographic medical scout image data. Also, in large systems where a large amount of data is taken it may be impractical or impossible for the operator of the medical system to do this as the tomographic medical scout image data is acquired.

In another embodiment the medical system further comprises a tomographic medical imaging system that is configured for acquiring medical imaging data from an imaging zone. The memory further comprises medical imaging system control commands configured for controlling the tomographic medical imaging system to acquire the tomographic medical scout image data.

Execution of the machine-executable instructions further causes the processor to acquire the tomographic medical scout image data by controlling the tomographic medical imaging system with the medical imaging system control commands. Execution of the machine-executable instructions further causes the processor to receive clinical scan planning data in response to acquiring the tomographic medical scout image data. The tomographic medical scout image data is descriptive of a first region. The clinical scan planning data is configured to modify the medical imaging system control commands to acquire clinical tomographic medical image data descriptive of a second region. The second region is within the first region. The clinical tomographic medical image data has higher resolution and/or higher signal to noise than the tomographic medical scout image data. The clinical tomographic medical image data may be for example acquired with a different acquisition protocol.

Execution of the machine-executable instructions further causes the processor to construct clinical control commands by modifying the medical imaging system control commands with the clinical scan planning data. Execution of the machine-executable instructions further causes the processor to acquire the clinical tomographic imaging data by controlling the medical imaging system with the clinical control commands.

This embodiment may have the benefit of examining the lower resolution tomographic medical scout image data. If automated systems were used to examine medical image data acquired by the tomographic medical imaging system the skilled person would first use the higher resolution data for doing the detection. This embodiment may provide the benefit of detecting anatomical deviations in the tomographic medical scout image data which is normally considered not useful for scanning for anatomical deviations.

In another embodiment the tomographic medical imaging system is a magnetic resonance imaging system.

In another embodiment the tomographic medical imaging system is a computed tomography system.

In another embodiment the tomographic medical imaging system is a combined computer tomography and positron emission tomography system.

In another embodiment the tomographic medical imaging system is a combined magnetic resonance imaging system and positron emission tomography system.

In another embodiment execution of the machine-executable instructions further causes the processor to receive an incidental scan indicator in response to providing the warning signal. The incidental scan indicator provides a selection of a discharge subject selector and an incidental scan selector. The incidental scan indicator is a control or flow indicator which causes a change in the behavior of the processor of the medical system. The incidental scan indicator may for example be a variable or indicator which chooses between a discharge subject selector and an incidental scan selector.

Execution of the machine-executable instructions further causes the processor to provide a discharge subject signal after completing acquisition of the clinical tomographic medical imaging data if the further scan indicator selects the discharge subject selector. In some examples the discharge subject signal may also be provided if the warning signal is not provided. The discharge subject signal may for example be a display or indicator on the medical system or may be a light indicator, bell or other indicator which may be useful for signaling the subject. The discharge subject signal may be used by the operator of the medical system to inform the subject being imaged that he or she may leave.

Execution of the machine-executable instructions further causes the processor to receive incidental scan planning data if the incidental scan indicator provides the incidental scan selector. This portion may function in several different ways. For example, an automated system may be used to provide the incidental scan planning data. For example, the localization may be used to set up a set of planes or regions to scan using the tomographic medical imaging system automatically. In other examples a user interface or dialogue box may be presented to the operator of the medical system and the operator may input the incidental scan planning data into a user interface of the medical imaging system. In yet other examples the incidental scan planning data may be appended to the incidental scan indicator. For example, if the incidental scan indicator has been received from a different workstation or remote location an automated system or medical professional may have already appended the incidental scan planning data to it.

In some examples if the third region is within an edge zone or portion of the first region then the machine executable instructions may be configured to acquire an additional tomographic medical scout image data. The machine executable instructions may for example be configured to choose an additional field of view for the additional tomographic medical scout image data such that the third region is within a central zone of the additional field of view.

This additional tomographic medical scout image data could in some examples be forwarded to the selected computing device also.

In another embodiment execution of the machine-executable instructions further causes the processor to construct incidental control commands by modifying the medical imaging system control commands with the incidental scan planning data. Execution of the machine-executable instructions further cause the processor to acquire the incidental tomographic medical imaging data by controlling the medical imaging system with the incidental control commands. This embodiment may be beneficial because it provides for the acquisition of the incidental tomographic medical imaging data.

In another embodiment the incidental scan planning data is descriptive of a third region. The third region is at least partially within the first region. The third region is at least partially disjoint from the second region.

In some embodiments the third region may include the region indicated by the localization of the anatomical deviation that was received from the anatomical detection module.

In another embodiment execution of the machine-executable instructions further cause the processor to send the warning signal to a selected computing device via a network connection. In this case the warning signal may comprise additional data. In some examples the warning signal may also comprise the anatomical deviation as well as the tomographic medical scout image data. Execution of the machine-executable instructions further causes the processor to receive the incidental scan indicator from the selected computing device via the network connection in response to sending the warning signal to the selected computing device. This embodiment may for example be beneficial because it may be useful for contacting a remote system or individual for providing the incidental scan indicator.

The selected computing device may take different forms. In one example it may be a smartphone. In another example it may be a computer or workstation used in a radiological department. In another example it may for example be a computer system located in a variety of locations. The computer system may for example be a desktop computer.

In another embodiment execution of the machine-executable instructions causes the warning signal to be sent to the selected computing device before completion of the acquisition of the clinical tomographic medical imaging data. This may be beneficial because it may provide the opportunity to provide further imaging of the subject before the subject has been discharged.

In another embodiment the medical system further comprises the selected computing device. The selected computing device comprises a display. The selected computing device is configured for displaying the warning signal automatically upon receipt. For example, the processor of the medical system may push the warning signal to the selected computing device and this may override other operations of the computing device such that it is brought immediately to the attention of the operator.

In another embodiment the memory comprises a list of allowed computing devices. Execution of the machine-executable instructions further causes the processor to poll the allowed computing devices for current user activity. The current user activity may for example be an indication of when the device or computing device was last used. The current user activity may also indicate the use of the allowed computing device. Execution of the machine-executable instructions further causes the processor to select the selected computing device from the allowed computing devices by applying a predetermined selection criterion to the current user activity. This may be particularly beneficial in receiving the incidental scan indicator promptly. For example, the list of allowed computing devices may be a list of allowed computing devices belonging to or operated by a particular physician. This may for example enable a physician to be contacted more rapidly and enable the incidental scan indicator to be received before the subject has been discharged.

In other examples the list of allowed computing devices may be computing devices used by a variety of medical professionals or physicians. This may then allow the medical system to automatically contact a physician or medical professional who is currently available. The predetermined selection criteria may also enable the system to contact a physician who is currently engaged in activity which would be acceptable for disturbing the physician or medical professional. For example, if the allowed computing device was a smartphone the predetermined selection criterion could look at the apps or app which is currently being operated by the smartphone. If the physician were currently reviewing emails or using a leisure time app then the predetermined selection criterion could then automatically determine to provide the warning signal to that particular computing device.

Another concrete example would be if the allowed computing device is a particular workstation in a radiology department. If this workstation is being currently used by a radiologist to review other medical imaging data then the system could be configured to automatically interrupt what the physician or healthcare professional is currently doing and provide the warning signal on the selected computing device. This may not only allow for receiving the incidental scan indicator more rapidly but it may also be less disruptive to the workflow of a particular healthcare professional or physician.

In another embodiment the anatomical detection module comprises a segmentation algorithm. The segmentation algorithm is adapted for detecting the anatomical deviation. For example, the segmentation algorithm could be used for detecting when the boundaries between two anatomical regions are irregular or misshapen. This could be used for triggering the warning signal and also the region which is triggering the warning signal may be used to provide the locator. In other examples, if a segmentation indicates that a particular anatomical region is larger or proportionally larger than expected, this may also trigger the warning signal. The segmentation algorithm may also detect anatomical structures which are not present within a particular model or anatomical atlas and therefore are outside of the scope of the segmentation algorithm. This may also trigger the warning signal.

In another embodiment the anatomical detection module comprises a neural network. The neural network is configured for outputting the localization of the anatomical deviation response to receiving the tomographic medical scout scan. For example, a neural network could be trained to look at the tomographic medical scout image data and provide a warning signal if the anatomical deviation is detected. The neural network could for example be a convolutional neural network. The neural network could be trained with a variety of scout scans that contain no anatomical deviations as well as some that are labeled with anatomical deviations. This may include various growths or abnormal structures. It may also include tomographic medical scout scans that have particular anatomical structures in the wrong location and/or are disproportionate size with respect to the other anatomical structures.

In another embodiment the neural network is a so-called U-net neural network. The use of a U-net neural network may be beneficial because the U-net neural network is able to correlate data on different spatial scales. This may be particularly useful in detecting the presence of anatomical deviations and for performing image segmentation.

In another aspect the invention provides for a computer program product comprising machine-executable instructions and an anatomical detection module. The machine-executable instructions are configured for being executed by a processor controlling a medical system. The anatomical detection module is configured for detecting an anatomical deviation in response to inputting a tomographic medical scout image data and outputting a localization of the anatomical deviation in the tomographic medical scout image data. Execution of the machine-executable instructions causes the processor to receive the tomographic medical scout image data.

Execution of the machine-executable instructions further causes the processor to receive the localization of the anatomical deviation from the anatomical detection module in response to inputting the tomographic medical scout image data into the anatomical detection module. Execution of the machine-executable instructions further causes the processor to provide a warning signal if the localization is received.

In another aspect the invention provides for a method of training the neural network. The method comprises receiving training data. The training data comprises training tomographic medical scout image data. The training data further comprises labels. The labels identify a localization of an anatomical deviation in the training tomographic medical scout image data. The method further comprises training the neural network with the label training data according to a deep learning algorithm.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiment's computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Tomographic medical image data is defined herein as two- or three-dimensional data that has been acquired using a medical imaging scanner. A medical imaging scanner is defined herein as an apparatus adapted for acquiring information about the physical structure of a patient and construct sets of two dimensional or three-dimensional medical image data. Tomographic medical image data can be used to construct visualizations which are useful for diagnosis by a physician. This visualization can be performed using a computer. Tomographic medical scout image data and clinical tomographic medical image data are both examples of tomographic medical image data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
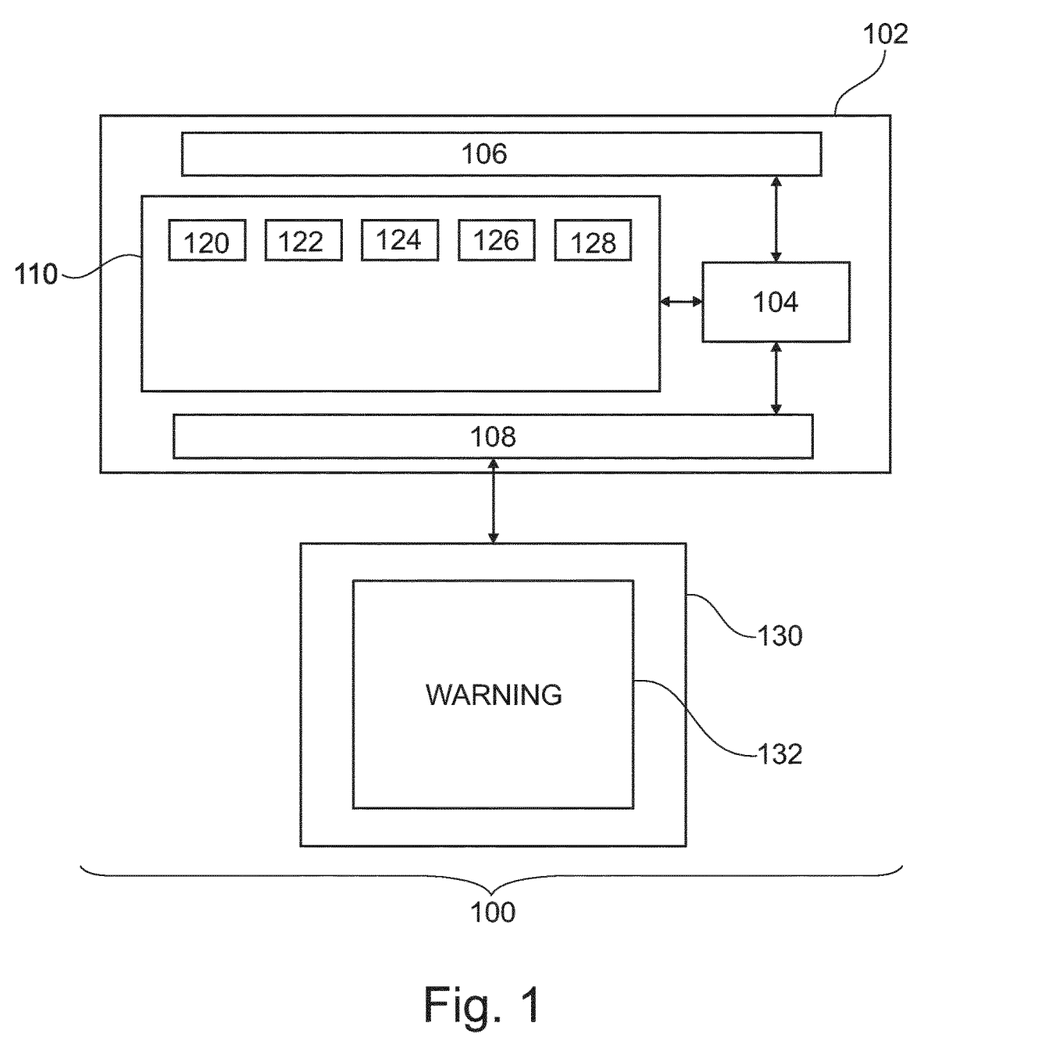
FIG. 1 illustrates an example of a medical system.

FIG. 1 illustrates an example of a medical system 100. The medical system 100 is shown as comprising a computer 102. In this example the medical system 100 is a workstation. Alternatively, the medical system 100 in this example could also be a remote server or processor within a cloud for processing medical image data.

The computer 102 is shown as containing a processor 104. The processor 104 is intended to represent one or more processing cores at one or more locations. The processors 104 could be distributed amongst multiple computers 102 that are possibly in different locations. The processor 104 is shown as being connected to an optional hardware interface 106. The hardware interface 106 may for example be used for controlling other components of the medical system 100. The processor 104 is also connected to an optional user interface 108. The processor 104 is further connected to a memory 110. The memory may be any memory or storage device which is accessible to the processor 104.

The memory 110 is shown as containing machine-executable instructions 120. The machine-executable instructions 120 contain instructions which enable the processor 104 to perform basic data and image processing tasks as well as also possibly controlling other components of the medical system 100 via the hardware interface 106. The memory 110 is further shown as containing an anatomical detection module. The anatomical detection module is configured for detecting an anatomical deviation in response to inputting a tomographic medical scout image data. If the anatomical deviation is detected then the anatomical detection module is configured for outputting a localization of the anatomical deviation within a tomographic medical scout image data.

The memory 110 is further shown as containing tomographic medical scout image data 124. The memory 110 is further shown as containing a localization of an anatomical deviation 126 within the tomographic medical scout image data 124 that was obtained by inputting the tomographic medical scout image data 124 into the anatomical detection module 122. The localization of the anatomical deviation 126 could for example be a location which is specified within the tomographic medical scout image data 124. In other examples it may be a segmentation. In response to receiving the localization of the anatomical deviation 126 a warning signal 128 has been generated. This warning signal 128 may be used to trigger a variety of actions. In this example the user interface 108 is shown as comprising a display 130. A warning message 132 is positioned on the display 130 to indicate to an operator that the anatomical deviation has been detected.

Figure 2:
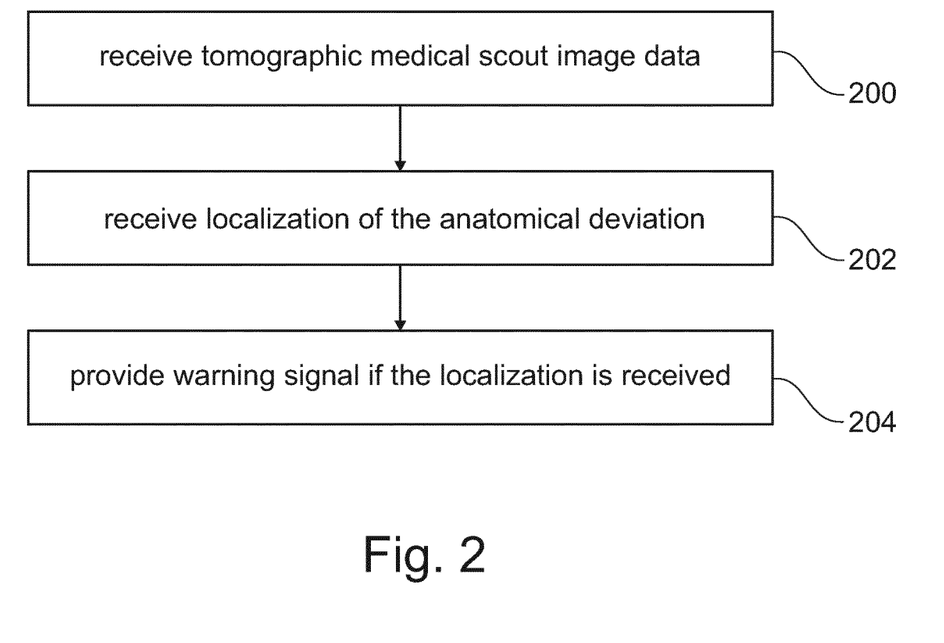
FIG. 2 shows a flow chart which illustrates an example of operating the medical system of FIG. 1.

FIG. 2 shows a flowchart which illustrates a method of operating the medical system of FIG. 1. The method starts with step 200. In step 200 the tomographic medical scout image data 124 is received. Next in step 202 the tomographic medical scout image data 124 is input into the anatomical detection module 122. If the anatomical detection module 122 detects an anatomical deviation then it outputs a localization of the anatomical deviation 126. In response the processor 104 then generates a warning signal 128 in step 204.

Figure 3:
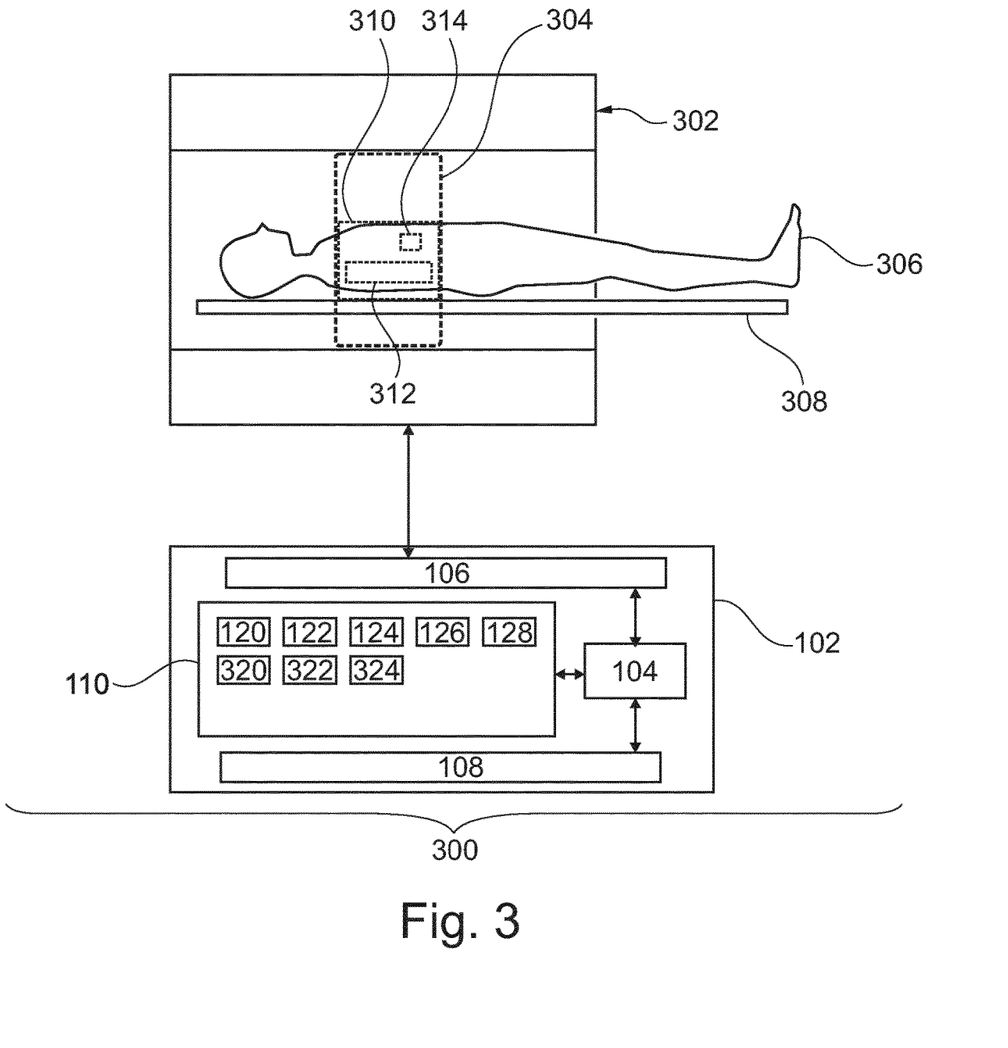
FIG. 3 illustrates a further example of a medical system.

FIG. 3 shows a further example of a medical system 300. The medical system 300 is similar to the medical system 100 of FIG. 1 except it additionally comprises a tomographic medical imaging system 302. The tomographic medical imaging system 302 of FIG. 3 is intended to be representative. It could for example be a magnetic resonance imaging system, a computed tomography system, a combined computer tomography and positron emission tomography system, or even possibly a combined magnetic resonance imaging system and positron emission tomography system.

The tomographic medical imaging system comprises an imaging zone 304. The imaging zone 304 is a region in space where the medical system 302 is able to measure medical imaging data. A subject 306 is shown as reposing on a subject support 308. The subject 306 is at least partially within the imaging zone 304. Within the imaging zone 304 is a first region 310, a second region 312, and a third region 314. The first region 310 corresponds to the region where the tomographic medical scout image data 124 is acquired from. The memory 110 further contains medical imaging system control commands 320 that may be used to control the tomographic medical imaging system 302 to acquire medical imaging data from any of the three locations 310, 312, or 314. In some examples the third region 314 may extend out of the first region 310.

The processor 104 may be configured for calculating clinical scan planning data 322. This may be modified to acquire clinical tomographic medical imaging data 324 from the second region 312. The third region 313 may represent a region of the subject 306 which contains an anatomical deviation. The localization of the anatomical deviation 126 may for example contain coordinates or a location of the third region 314. In response to receiving the tomographic medical scout image data 124 clinical scan planning data 322 may be generated. The clinical scan planning data 322 may for example either be manually input into the user interface 108 or it may be generated using an automated algorithm or neural network. The clinical scan planning data 322 may be used for modifying the medical imaging system control commands 320 to acquire the clinical tomographic medical imaging data 324.

Figure 4:
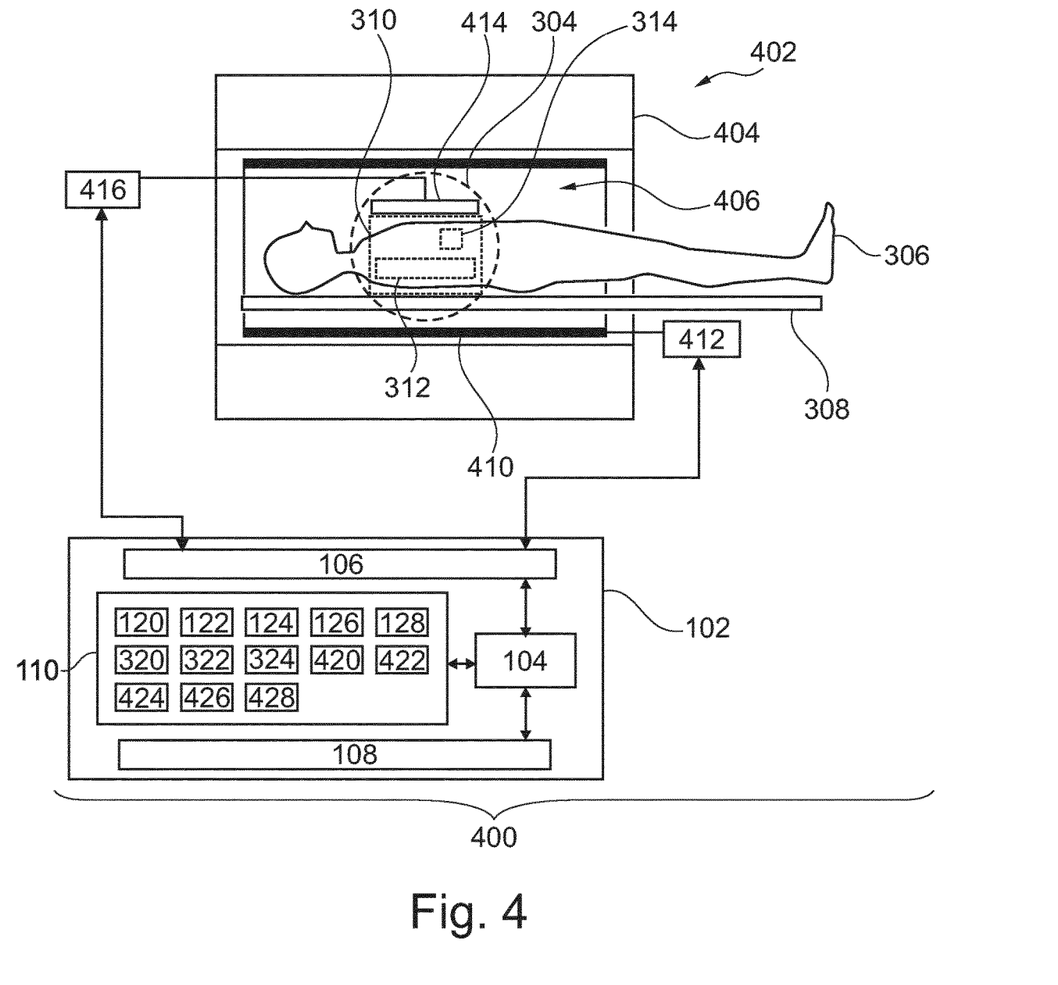
FIG. 4 illustrates a further example of a medical system.

FIG. 4 illustrates a further example of a medical system 400. The example illustrated in FIG. 4 is similar to that illustrated in FIG. 3 except tomographic medical imaging system 302 is specifically a magnetic resonance imaging system 402.

The magnetic resonance imaging system 402 comprises a magnet 404. The magnet 404 is a superconducting cylindrical type magnet with a bore 406 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 406 of the cylindrical magnet 404 there is an imaging zone 304 where the magnetic field is strong and uniform enough to perform magnetic resonance imaging. The first region 310, the second region 312 and the third region 324 in this example may be considered to be regions of interest (ROIs). The magnetic resonance data that is acquired typically acquired for the region of interest.

Within the bore 406 of the magnet there is also a set of magnetic field gradient coils 410 which is used for acquisition of preliminary magnetic resonance data to spatially encode magnetic spins within the imaging zone 408 of the magnet 404. The magnetic field gradient coils 410 connected to a magnetic field gradient coil power supply 412. The magnetic field gradient coils 410 are intended to be representative. Typically magnetic field gradient coils 410 contain three separate sets of coils for spatially encoding in three orthogonal spatial directions. A magnetic field gradient power supply supplies current to the magnetic field gradient coils. The current supplied to the magnetic field gradient coils 410 is controlled as a function of time and may be ramped or pulsed.

Adjacent to the imaging zone 304 is a radio-frequency coil 414 for manipulating the orientations of magnetic spins within the imaging zone 304 and for receiving radio transmissions from spins also within the imaging zone 304. The radio frequency antenna may contain multiple coil elements.

The radio frequency antenna may also be referred to as a channel or antenna. The radio-frequency coil 414 is connected to a radio frequency transceiver 416. The radio-frequency coil 414 and radio frequency transceiver 416 may be replaced by separate transmit and receive coils and a separate transmitter and receiver. It is understood that the radio-frequency coil 414 and the radio frequency transceiver 416 are representative. The radio-frequency coil 414 is intended to also represent a dedicated transmit antenna and a dedicated receive antenna. Likewise the transceiver 416 may also represent a separate transmitter and receivers. The radio-frequency coil 414 may also have multiple receive/transmit elements and the radio frequency transceiver 416 may have multiple receive/transmit channels. For example if a parallel imaging technique such as SENSE is performed, the radio-frequency could 414 will have multiple coil elements.

The transceiver 416 and the gradient controller 412 are shown as being connected to the hardware interface 106 of the computer system 102.

In this example the medical imaging system control commands are pulse sequence commands and the clinical tomographic medical imaging data 324 and tomographic medical scout image data 124 are both magnetic resonance images.

The memory is further shown as comprising an incidental scan indicator 420. This may for example have been received via the user interface 108 or for example via a network connection. The memory 110 is further shown as containing incidental scan planning data 422. This for example may be used to acquire incidental tomographic medical imaging data 426 from the third region 314. In some instances, the incidental scan planning data 422 may be entered manually. In other cases, it may be generated by an automated scan planning module 428.

Figure 5:
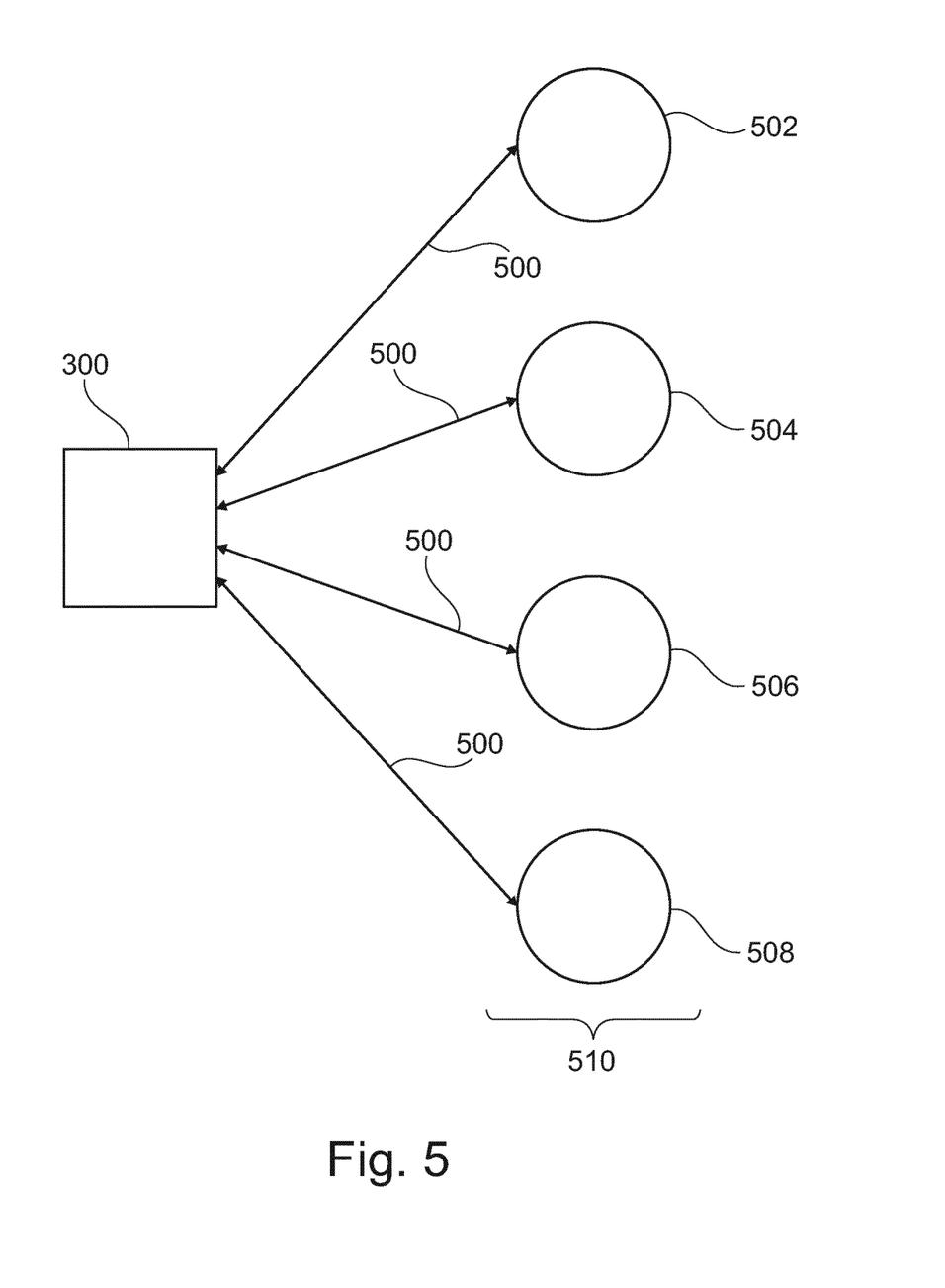
FIG. 5 illustrates a further example of a medical system.

FIG. 5 shows a further view of the medical system 300 of FIG. 3. The medical system 300 may also be replaced by the medical system 400. In this example the medical system 300 is connected via network interfaces 500 to a variety of computing devices, for example a smartphone 502, a mobile computing device 504, a workstation 506, and a desktop computer 508. These devices 602, 604, 606, 608 are examples of allowed computer devices 610. They for example may be work or personal computing devices of a medical professional or physician. When the medical system 300 detects an anatomical deviation and provides the warning signal 128 the medical system 300 may forward the warning signal to one of the devices 502, 504, 506, 508. In response it may receive the incidental scan indicator 420 from one of the devices.

In some examples the medical system 300 may poll each of the allowed computing devices 610 to determine a current user activity. Using a predetermined selection criterion, a device 502, 504, 506, 508 may be selected from the allowed computing devices 610. This may for example allow for a quicker response as well as more efficient use of the time of the physician or healthcare professional using one of the devices.

Figure 6:
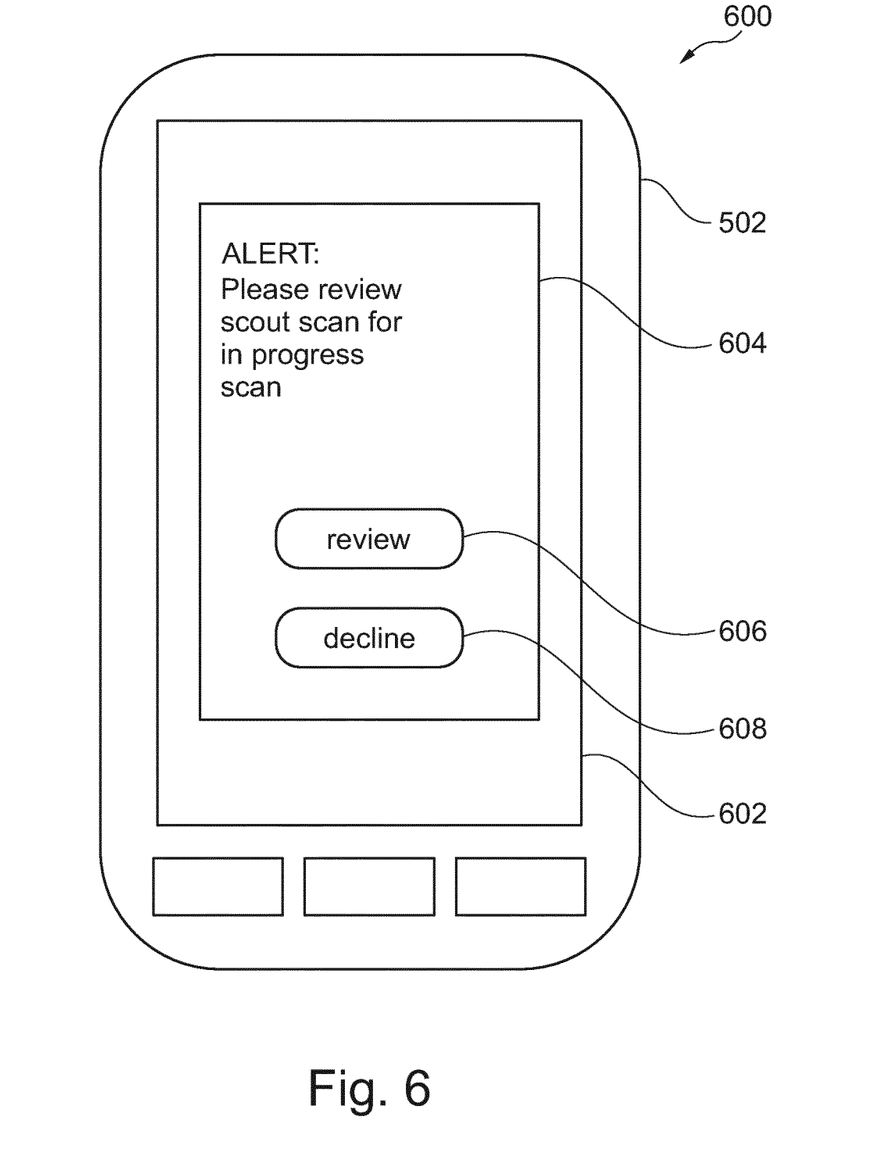
FIG. 6 illustrates a further example of a medical system.

FIG. 6 shows a further view of the smartphone 502. When the warning signal was generated by the medical system 300 the system determined that the physician owning the smartphone 502 was currently using email. In response the medical system 300 sent the warning signal to the smartphone 502. In this case the smartphone 502 is the selected computing device 600. This then causes an alert message 604 to be displayed on the user interface 602 of the smartphone 502. There are then for example two buttons which are presented, one which is a review now button 606 and a decline review 608. If the review now button 606 is pressed then data which is descriptive of the scout scan as well as providing the localization are displayed on the user interface 602. From this the physician or healthcare professional can then provide the incidental scan indicator 420. The incidental scan indicator 420 in some instances may just indicate whether to scan the third region or not. In other instances, it may provide more detailed instructions on how to perform a further scan.

When making an Magnetic Resonance (MR) scan of, e.g., the lumbar spine, a scout or localizer scan (e.g. T1 weighted low resolution scan; three orthogonal planes) is initially taken and used to plan the geometry of the diagnostic images. The scout scan might reveal incidental findings such as a renal tumor or an aortic aneurysm that are not properly visualized in the diagnostic images (e.g. because of the field-of-view). Typically, the incidental findings are not detected until the study is interpreted, subsequent to the scanning episode. Occasionally, the findings are not even detected as they are only visible on the low resolution, and typically ignored, scout images. As a result, either the incidental findings are missed or, if detected, the patient must be invited for another scanning session.

Examples may combine one or more of the following features:
1. design an MR exam card that includes 1. higher contrast and/or spatial resolution which offers the opportunity for improved sensitivity at identifying incidental findings on scout views and 2. improved spatial coverage that enhance the chances of including common incidental findings (e.g. renal, aortic, ovarian),
2. detect classes (e.g. renal, aortic, ovarian) of incidental findings in the MR scout scans (using e.g. neural networks or model-based approaches) and determine the potential need for an additional MR series, and
3. in the case of a potential need of an additional MR series, to trigger rapid bi-directional communication of scout images and automatically generated reviews of such images to a radiologist (e.g. directly on premises or via remote/cloud-based means (e.g. teleradiology)) to review quickly while the patient is still on the MR scanner, in order to enable additional scans,
4. inform the operator of the MR scanner via a message whether the patient can be released, a decision for an additional MR series is pending or an additional scan should be performed, and
5. automatically initiate acquisition of the additional MR series when required. Steps 2 and 3 are done after acquisition of the scout scan during the time that the remainder of the MR scan is performed, in order that the incidental findings might be detected prior to the patient leaving the MR suite, in the event that additional imaging be acquired, if appropriate, at the same setting.

Example medical systems may be integrated with MR scanner consoles or other tomographic imaging system consoles.

MR imaging of the lumbar spine is among the most common MR examinations requested, second only to brain MR. Commonly, the study is read by a radiologist, and often by a neuroradiologist or musculoskeletal radiologist. As is typical of many imaging examinations, the lumbar spine MR is often an exam that once completed, if no surgical disease is found, either medical treatment consisting of pharmacologic and/or non-pharmacologic therapies (e.g. physical therapy) or no therapy is provided to the patient. In either scenario, it may be that the lumbar spine MR is the only advanced imaging that may be performed (plain radiographs are also commonly performed).

Occasionally, incidental findings are disclosed on the MR lumbar spine exam, and the radiologist is the gatekeeper at that point. If the findings are of little significance, they are barely included in the findings of the report. If the incidental findings are of greater import, such findings are commonly listed in the impression (conclusion) of the imaging report, and are commonly reported by phone, text, or other methodology, to the referring physician/provider. Unfortunately, if the findings are not observed and reported, and if the lumbar spine MR proves to be the only examination performed during the work up, it is possible that the incidental finding (e.g. renal/ureteral tumor, abdominal aortic aneurysm, ovarian mass, adrenal mass, etc.) will be allowed to progress: i.e. a missed opportunity scenario.

Thus, it would be helpful to establish a system of raising the odds of a positive outcome, whereby the incidental lesion is 1. Detected, 2. Reported and 3. Acted upon, offering the patient the optimal opportunity for a good outcome despite an otherwise incidentally discovered significant health threat. Even more helpful would be such a system that allows for automatic detection and reporting to that radiologist while the patient is still undergoing the examination, such that the remainder of the MR examination can be tailored to include not only the initial "target", the lumbar spine, but also the region of the incidentally discovered abnormality.

When making an MR scan of, e.g., the lumbar spine, a scout or localizer scan (e.g. T1 weighted low resolution scan; three orthogonal planes) is initially taken and used to plan the geometry of the diagnostic images that should be acquired.

The scout scan might reveal incidental findings (up to 20% of routine MRI examinations of the lumbar spine) and, depending on their location, they might not be visible in the diagnostic MR images. Often, a renal or adrenal kidney mass would, for instance, not be visible in the diagnostic MR images, because only a small part of the kidney is covered. Also, an aortic aneurysm might not be visible in the diagnostic MR images, because of the presaturation band. In these two examples, the findings might, and often are, included on the scout images. Some of these findings are subsequently observed at the time of interpretation; others unfortunately may go undetected. If observed, such patients may be invited for an additional scanning session.

In many cases, it would be desirable to avoid such additional sessions. Such sessions are inconvenient for all parties. Additionally, they incur additional expense, partly from the additional scan and interpretation (i.e. technical and professional fees) and partly from the workflow disruptions to both the patient and the physician and practice environment (e.g. imaging center). In the fee for service world, some may argue in favor of the additional billing; in the value-based world, such additional efforts are completely expense-based, to be subtracted from pre-negotiated managed care contracts.

Examples may provide for an alternative to the common pathway that ideally allows for more timely recognition of incidental findings, such that the decision-making related to the findings can be engaged while the patient is still on the scanner couch. In particular, examples may allow to reduce the necessity to recall patients for a further imaging session in the case that the scout scans reveal incidental findings.

Examples also potentially allows for the introduction of some degree of artificial/augmented intelligence or deep learning algorithm to improve the sensitivity and potentially specificity of detecting such findings.

Examples may incorporate one or more of the following features:

1. to design an MR exam card that includes 1. higher contrast and/or spatial resolution which offers the opportunity for improved sensitivity at identifying incidental findings on scout views and 2. improved spatial coverage that enhance the chances of including common incidental findings (e.g. renal, aortic, ovarian),
2. to detect classes (e.g. renal, aortic, ovarian) of incidental findings in the MR scout scans (using e.g. neural networks or model-based approaches) and determine the potential need for an additional MR series, and
3. in the case of a potential need of an additional MR series, to trigger rapid bi-directional communication of scout images and automatically generated reviews of such images to a radiologist (e.g. directly on premises or via remote/cloud-based means (e.g. teleradiology)) to review quickly while the patient is still on the MR scanner, in order to enable additional scans,
4. to inform the operator of the MR scanner via a message whether the patient can be released, a decision for an additional MR series is pending or an additional scan should be performed, and
5. to automatically initiate acquisition of the additional MR series when required. Steps 2 and 3 are done after acquisition of the scout scan during the time that the remainder of the MR scan is performed, in order that the incidental findings might be detected prior to the patient leaving the MR suite, in the event that additional imaging be acquired, if appropriate, at the same setting. In the ideal case, steps 2 and 3 can be completed before the patient's previously planned imaging has been accomplished.

The different steps in the workflow and the technical means applied in the different steps are explained in the following at the example of a lumbar spine MRI scan. As sample protocol, we assume that the standard MR protocol includes axial T1-weighted slices using a pre-saturation band and a geometry.

Figure 7:
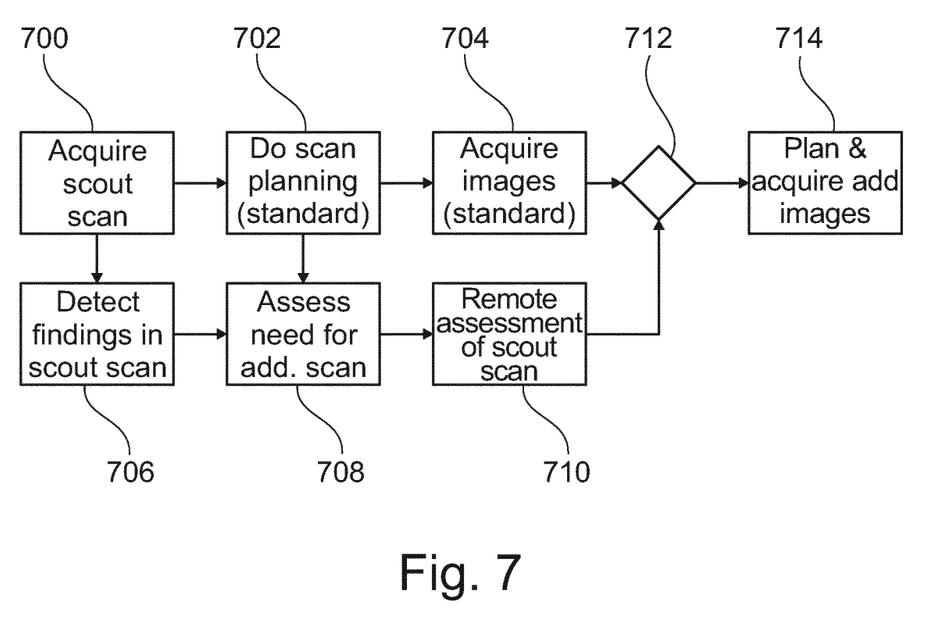
FIG. 7 shows a flow chart which illustrates a further example of operating a medical system.

FIG. 7 illustrates a further example of a method. The method starts with step 700 where a scout scan is acquired. Next in step 702 using the scout scan, scan planning is performed. This may for example be an automated or manual system. After the scout scan has been acquired step 706 is performed in parallel. In step 706 you detect findings in the scout scan which is equivalent to detecting anatomical deviation. After step 706 and 702 are performed step 708 is performed. In step 708 an assessment is determined if there is an additional scan which is needed. For example, if the localization of the anatomical deviation is within the range of the scan planned in step 702 it may not be necessary. After step 702 is performed step 704 is performed. This is to acquire the normal medical images; this is equivalent to acquiring the clinical tomographic medical image data. After step 708 is performed the remote assessment of the scout scan 710 is performed. In step 712 information is provided for the operator. Finally, in step 714, additional images are planned and acquired. These steps are discussed in greater detail below:

700—Acquire Scout Scan

Initially a scout or localizer scan is acquired. The scout scan is, for instance, a T1-weighted low-resolution scan with three orthogonal planes. The scout scan covers a larger region than the lumbar spine and shows, for instance, the kidney and possibly the femoral heads. The scout scan is subsequently used for scan planning and processed to detect extraspinal findings. Detection of the incidental findings might be done on the system where scan planning is performed. Alternatively, the scout scans are sent to a server or a cloud performing the detection of incidental findings.

A pre-requisite of identifying incidental findings in scout scans is a sufficient image quality in terms of contrast, spatial resolution and spatial coverage. To achieve this, in one embodiment scout images are again obtained, although taking advantage of both enhanced pre-scan localization techniques, such as camera-based identification of expected anatomic locations, and technical improvements, such as compressed sensing, which allows for acceleration of image acquisition. This latter time saving can be deployed either to increase the number of scout images obtained during the same period of time or to enhance image contrast and spatial resolution, or some of both. According to such a paradigm, improved acquisition of scout images is affected.

702—Perform Scan Planning

Using the scout scan, the acquisition of the images that should be acquired is defined. For the specific example, this means that the geometry of the axial slices and the pre-saturation band is defined.

In case an incidental finding has been detected (step 706), the system might show the detected finding during scan planning and offer the option to properly extend the scanning geometry (e.g. additional axial image slices) to cover the region of the incidental finding.

704—Acquire Image

After completion of the scan planning, the MR images (standard) are acquired.

706—Detect Findings in Scout Scan

Using a sufficiently large amount of annotated scout scans as basis for learning, a neural network (e.g. a U-net) can be trained and used to localize and segment the (left or right) kidney in the transversal scout scans. If the (left or right) kidney is seen within the image, a further neural network can be trained and used to classify whether and what kind of abnormality the kidney shows. Techniques like Monte-Carlo drop out can be used to derive a certainty associated with the finding.

Alternatively, deformable models or active shape models can be used to segment a kidney in the scout scan. Tumors or other abnormalities may then be identified by analyzing the kidney shape or the intensity distribution inside the kidney.

As a result of this processing step, the location of the kidney in the (transversal) scout scan is known together with an indication and certainty of the presence of an abnormality. This and similar approaches can also be applied to other, non-kidney related incidental findings.

In addition, specific imaging protocols (MR series information) are associated with each class of incidental finding. For instance, axial T1- and T2-weighted image stacks covering the kidneys may be proposed as additional MR series in case of incidental findings related to the kidney.

708—Assess Need for an Additional Scan

Depending on the type of finding, the certainty and the classification (clinical significance), the need for an additional scan and/or the remote assessment of the scout scan by a radiologist is determined. Within this step, the system may also use information about the planned imaging geometry (step 702), the location of the detected finding and needs for imaging the detected finding (MR sequence).

Three cases can be envisaged in this context:

No additional scan & no remote assessment. This option should, for instance, be selected if no finding is detected with high certainty or the detected findings have no clinical relevance with a large certainty.

Additional scan. This option should, for instance, be selected if a clinically relevant finding has been detected with high certainty, the protocol for imaging is clear and the additional effort for imaging is limited (e.g. no additional contrast agent required).

Remote assessment. This option should be selected for the other cases.

The parameters and thresholds associated with the decision may, for instance, be optimized with respect to the additional cost inferred by the remote assessment of the scout scans vs. the cost savings associated with making additional scans in a single session.

710—Remote Assessment of the Scout Scan

Depending on the outcome of step 708, a request to read the scout images and automatically generated reviews of such images by a radiologist is generated. As a response, the system receives information entered by the radiologist whether an additional MR series should be acquired or not and what MR series should be acquired. The system might propose a (list of) suitable imaging protocols that is derived from the detected findings.

712—Information for Operator

The system informs the operator regarding the status of the incidental findings assessment. In particular, the system indicates whether acquisition is completed and the patient can leave the scanning room or information about the additional scan that should be planned and acquired.

Though in some cases step 6 has been completed before the patient's previously planned imaging has been accomplished, the system might also show whether the response of step 6 is still pending.

714—Plan and Acquire Additional Images

In the case that an additional MR series is requested, respective information is obtained automatically from step 6 and the operator can plan and acquire the requested scan. For instance, if an abnormality has been detected in the kidneys, the system asks to plan axial T1- and T2-weighted image stacks covering the kidneys. The system may indicate the location of the suspected lesion or highlight the kidney to support positioning of the axial slice stack. In addition, the system might add an additional margin above and below the kidney to account for an uncertainty of the kidney position due to respiratory excursion. After completion of planning the additional MR series, the images are acquired.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or

| | LIST OF REFERENCE NUMERALS |
|---|---|
| 100 | medical system |
| 102 | computer |
| 104 | processor |
| 106 | hardware interface |
| 108 | user interface |
| 110 | memory |
| 120 | machine executable instructions |
| 122 | anatomical detection module |
| 124 | tomographic medical scout image data |
| 126 | localization of anatomical deviation |
| 128 | warning signal |
| 130 | display |
| 132 | warning message |
| 200 | receive the tomographic medical scout image data |
| 202 | receive the localization of the anatomical deviation from the anatomical detection module in response to inputting tomographic medical detection module into the anatomical detection module |
| 204 | provide a warning signal if the localization is received. |
| 300 | medical system |
| 302 | tomographic medical imaging system |
| 304 | imaging zone |
| 306 | subject |
| 308 | subject support |
| 310 | first region |
| 312 | second region |
| 314 | third region |
| 320 | medical imaging system control commands |
| 322 | clinical scan planning data |
| 324 | clinical tomographic medical imaging data |
| 400 | medical system |
| 402 | magnetic resonance imaging system |
| 404 | magnet |
| 406 | bore of magnet |
| 410 | magnetic field gradient coils |
| 412 | magnetic field gradient coil power supply |
| 414 | radio-frequency coil |
| 416 | transceiver |
| 420 | incidental scan indicator |
| 422 | incidental scan planning data |
| 424 | incidental control commands |
| 426 | incidental tomographic medical imaging data |
| 428 | automated scan planning module |
| 500 | network connection |
| 502 | smart phone |
| 504 | mobile computing device |
| 506 | workstation |
| 508 | desk top computer |
| 510 | list of allowed computing devices |
| 600 | selected computing device |
| 602 | user interface |
| 604 | altert message |
| 606 | review now button |
| 608 | decline review button |
| 610 | allowed computer devices |
| 700 | Acquire scout scan. |
| 702 | Perform scan planning |
| 704 | Acquire image |
| 706 | Detect findings in scout scan |
| 708 | Assess need for an additional scan |
| 710 | Remote assessment of the scout scan |
| 712 | Information for operator |

The invention claimed is:

1. A medical system comprising:
a tomographic medical imaging system configured to acquire medical imaging data from an imaging zone;
a memory configured to store machine executable instructions and medical imaging system control commands configured to control the tomographic medical imaging system to acquire tomographic medical scout image data;
an anatomical detection module, wherein the anatomical detection module is configured to detect an anatomical deviation in response to inputting tomographic medical scout image data, wherein the anatomical detection module is configured to output a localization of the anatomical deviation in the tomographic medical scout image data if the anatomical deviation is detected;
a processor configured to control the medical system, wherein execution of the machine executable instructions causes the processor to:
acquire the tomographic medical scout image data by controlling the tomographic medical imaging system with the medical imaging system control commands;
receive clinical scan planning data in response to acquiring the tomographic medical scout image data, wherein the tomographic medical scout image data is descriptive of a first region, wherein the clinical scan planning data is configured to modify the medical imaging system control commands to acquire clinical tomographic medical image data descriptive of a second region, wherein the second region is within the first region, wherein the clinical tomographic medical image data has a higher resolution than the tomographic medical scout image data;
construct clinical control commands by modifying the medical imaging system control commands with the clinical scan planning data; and
acquire the clinical tomographic medical imaging data by controlling the medical imaging system with the clinical control commands;
input the tomographic medical scout image data into the anatomical detection module;
receive the localization of the anatomical deviation from the anatomical detection module in response to inputting the tomographic medical scout image data into the anatomical detection module;
provide a warning signal if the localization is received;
receive an incidental scan indicator from a physician or healthcare professional either via a user interface in response to providing the warning signal or from a selected computing device via a network connection in response to sending the warning signal to the selected computing device, wherein the incidental scan indicator provides a discharge subject selector or an incidental scan selector;
provide a discharge subject signal after completing acquisition of the clinical tomographic medical imaging data if the incidental scan indicator provides the discharge subject selector;
receive incidental scan planning data if the incidental scan indicator provides the incidental scan selector.

2. The medical system of claim 1, wherein the tomographic medical imaging system is any one of the following: a magnetic resonance imaging system, a computed tomography system, a combined computed tomography and positron emission tomography system, and a combined magnetic resonance imaging system and positron emission tomography system.

3. The medical system of claim 1, wherein execution of the machine executable instructions further causes the processor to:
construct incidental control commands by modifying the medical imaging system control commands with the incidental scan planning data; and
acquire the incidental tomographic medical imaging data by controlling the medical imaging system with the incidental control commands.

4. The medical system of claim 1, wherein the incidental scan planning data is descriptive of a third region, wherein the third region is at least partially within the first region, and wherein the third region is at least partially disjoint from the second region.

5. The medical system of claim 1, wherein execution of the machine executable instructions causes the warning signal to be sent to the selected computing device before completion of the acquisition of the clinical tomographic medical imaging data.

6. The medical system of claim 1, wherein the medical system comprises the selected computing device, wherein the selected computing device comprises a display, and wherein the selected computing device is configured to display the warning signal automatically upon receipt.

7. The medical system of claim 1, wherein the memory comprises a list of allowed computing devices, wherein execution of the machine executable instructions further causes the processor to:
poll the allowed computing devices for current user activity; and
select the selected computing device from the allowed computing devices by applying a predetermined selection criterion to the current user activity.

8. The medical system of claim 7, wherein the current user activity is an indication of when each of the allowed computed devices were last used and/or a current user activity for each of the allowed computing devices.

9. The medical system of claim 7, wherein at least one of the allowed computing devices is a smartphone, wherein the predetermined selection criterion for selection of the smartphone is the usage of an email app or a leisure time app.

10. The medical system of claim 7 wherein at least one of the allowed computing devices is a radiology workstation, wherein the predetermined selection criterion for selection of the radiology workstation is the usage of the worstation for the review of other medical imaging data.

11. The medical system of claim 1, wherein the anatomical detection module comprises a segmentation algorithm, wherein the segmentation algorithm is adapted to detect the anatomical deviation.

12. The medical system of claim 1, wherein the anatomical detection module comprises a neural network, and wherein the neural network is configured for outputting the localization of the anatomical deviation in response to receiving the tomographic medical scout scan.

13. The medical system of claim 12, wherein the neural network is a U-Net neural network and/or wherein the trained neural network is trained according to the following method:
receiving training data, wherein the training data comprises training tomographic medical scout image data, wherein the training data further comprises labels, wherein the labels identify a localization of an anatomical deviation in the training tomographic medical scout image data wherein; and
training the neural network with the labeled training data according to a deep learning algorithm.

14. A computer program product comprising machine executable instructions stored on a non-transitory computer readable medium and an anatomical detection module, wherein the machine executable instructions are configured to be executed by a processor that controls a medical system, wherein the medical system comprises a tomographic medical imaging system configured to acquire medical imaging data from an imaging zone, wherein the anatomical detection module is configured to detect an anatomical deviation in response to inputting tomographic medical scout image data, wherein the anatomical detection module is configured to output a localization of the anatomical deviation in the tomographic medical scout image data if the anatomical deviation is detected, wherein execution of the machine executable instructions causes the processor to:
acquire the tomographic medical scout image data by controlling the tomographic medical imaging system with medical imaging system control commands, wherein the medical imaging system control commands are configured to control the tomographic medical imaging system to acquire the tomographic medical scout image data;
receive clinical scan planning data in response to acquiring the tomographic medical scout image data, wherein the tomographic medical scout image data is descriptive of a first region, wherein the clinical scan planning data is configured to modify the medical imaging system control commands to acquire clinical tomographic medical image data descriptive of a second region, wherein the second region is within the first region, wherein the clinical tomographic medical image data has a higher resolution than the tomographic medical scout image data;
construct clinical control commands by modifying the medical imaging system control commands with the clinical scan planning data; and
acquire the clinical tomographic medical imaging data by controlling the medical imaging system with the clinical control commands;
input the tomographic medical scout image data into the anatomical detection module;
receive the localization of the anatomical deviation from the anatomical detection module in response to inputting the tomographic medical scout image data into the anatomical detection module; and
provide a warning signal if the localization is received;
receive an incidental scan indicator from a physician or healthcare professional either via a user interface in response to providing the warning signal or from a selected computing device via a network connection in response to sending the warning signal to the selected computing device, wherein the incidental scan indicator provides a selection of a discharge subject selector or an incidental scan selector;
provide a discharge subject signal after completing acquisition of the clinical tomographic medical imaging data if further scan indicator selects the discharge subject selector;
receive incidental scan planning data if the incidental scan indicator provides the incidental scan selector.

* * * * *